United States Patent [19]

Oshlack et al.

[11] Patent Number: 5,217,965

[45] Date of Patent: Jun. 8, 1993

[54] STABILIZED SOLID DOSAGE FORMS OF CHOLINE METAL CARBOXYMETHYLCELLULOSE SALICYLATE COMPOSITIONS

[75] Inventors: Benjamin Oshlack, New York; Frank C. Pedi, Jr., Yorktown Heights, both of N.Y.; Joseph V. Zirlis, Branford, Conn.

[73] Assignee: Euroceltique, S.A., Luxembourg

[21] Appl. No.: 716,547

[22] Filed: Jun. 17, 1991

[51] Int. Cl.$^5$ .................. A61K 31/60; A61K 47/00
[52] U.S. Cl. .................. 514/160; 514/165; 514/781; 514/960; 514/970
[58] Field of Search ........... 514/166, 158, 165, 961, 514/970, 160

[56] References Cited

U.S. PATENT DOCUMENTS 4,067,974 1/1978 Sasmor .................. 424/231
5,043,168 8/1991 Patel .................. 424/682

OTHER PUBLICATIONS

Chemical Abstracts 109(18):156086(n) Rowe.
Chemical Abstracts 106(24): 201635(s)–Vander Watt.

Primary Examiner—S. J. Friedman
Assistant Examiner—T. J. Criares
Attorney, Agent, or Firm—Steinberg & Raskin

[57] ABSTRACT

The stability of compositions of choline salicylate-metal salicylate-carboxymethylcellulose is improved by the incorporation therein of microcrystalline cellulose. The microcrystalline cellulose is linked to the remainder of the composition by liquid bridges and is preferably present in an amount of about 2.5-25% by weight. The microcrystalline cellulose enhances the stability of the composition and thereby enhances solid dosage forms thereof such as tablets, capsules, suppositories and granules.

21 Claims, No Drawings

STABILIZED SOLID DOSAGE FORMS OF CHOLINE METAL CARBOXYMETHYLCELLULOSE SALICYLATE COMPOSITIONS

BACKGROUND OF THE INVENTION

Choline salicylate, a well-known analgesic, which is highly hygroscopic, has been prepared in pharmaceutically acceptable, solid dosage forms, by means of a salicylate of a metal having a valence of at least 2, such as aluminum, bismuth, calcium or magnesium. It has further been shown that such composition is stabilized to a greater extent by the addition thereto of carboyxmethylcellulose. All of the above is described in U.S. Pat. No. 4,067,974.

While the compositions of U.S. Pat. No. 4,067,974 constitute a considerable improvement over older choline salicylate compositions, a need has been found to improve the stability of pharmaceutical preparations thereof which are solid in nature, such as tablets, capsules, suppositories and granules.

SUMMARY OF THE INVENTION

It is accordingly a primary objection of the present invention to provide improved stability for choline metal carboxymethylcellulose salicylate compositions, wherein the metal has a valence of at least 2, such as aluminum, bismuth, calcium or magnesium salicylate.

It is yet another object of the present invention to improve the stability of solid compositions of choline salicylate plus a salicylate of a physiologically compatible metal having a valence of at least 2 plus a carboxy lower alkyl cellulose such as carboxymethylcellulose.

Other objects and advantages of the present invention will be apparent from the further reading of the specification and of the appended claims.

With the above and other objects in view, the present invention mainly comprises the addition to a composition of choline salicylate, a salicylate of a physiologically compatible metal having a valence of at least 2 and a carboxy lower alkyl cellulose of a stabilizing effective amount of microcrystalline cellulose (MCC).

As described in U.S. Pat. No. 4,067,974, the stabilizing effective amount of the carboxymethylcellulose (CMC) for the choline salicylate-metal salicylate, is between about 2.5–25% by weight.

It has been found according to the present invention that the addition to the composition of choline salicylate-metal salicylate-carboxymethylcellulose of microcrystalline cellulose, preferably in an amount of 2.5–25% by weight, enhances the stabilization of the composition so as to enhance solid dosage forms thereof, such as tablets, capsules, suppositories and granules.

The microcrystalline cellulose used according to the present invention should preferably have a size between about 60 mesh and 400 mesh, preferably between about 60 mesh and 200 mesh, with less than 1% of the particles having a size larger than the selected mesh size.

Several interesting phenomena have been noted in connection with the present invention.

The addition of MCC cellulose to a choline salicylate-metal salicylate composition without the CMC being present does not result in any increased stabilization.

The use of additional CMC instead of MCC cellulose does not result in any improved stabilization.

The addition of other common pharmaceutical dosage binders, such as polyvinylpyrrolidone, acrylic resins, methocel, fatty acids, hydrogenated oils, and the like do not further enhance the stability of the composition.

The incorporation of the MCC in a dry mix with the choline salicylate-metal salicylate-carboxymethylcellulose composition in a dry mix does not result in any significant enhancement of the stability of the solid dosage form.

The stability of the solid dosage form is enhanced by means of the MCC only if the MCC is mixed with the remainder of the composition under wet conditions either during the formation of the cholie metal carboxymethylcellulose salicylate composition or by mixing the MCC with the composition under wet conditions. In other words, the stability of the composition is increased only by the formation of liquid bridges between the MCC and the choline metal carboxymethylcellulose salicylate composition. Simple dry mixing, even by means of fluidized solid bed, will not result in improved stability.

The liquid bridge between the MCC and the choline metal carboxymethylcellulose salicylate composition needed to achieve the improved stability of the present invention is of the type described in the "The Effect of the Wet Granulation Process of Drug Dissolution" of H. M. Unvala, et al., in Drug Development and Industrial Pharmacy, Vol. 14, No. 10, 1327–1349 (1988).

The stabilized choline metal carboxymethylcellulose salicylate compositions with the MCC in accordance with the present invention can be converted into convenient solid dosage forms such as tablets, capsules, granules, suppositories and the like for administration to humans and animals for salicylate/choline salicylate therapy.

A further advantage of the compositions of the present invention is that whereas solid dosage forms of solidified choline metal salicylate prior to the present invention required large quantities of excipients to provide stabilized solid dosage forms, the use of MCC according to the present invention significantly reduces the size of the final solid dosage form product.

The new solid dosage forms of choline salicylate-metal salicylate-carboxymethycellulose-MCC display improved tabletting qualities in terms of hardness, disintergration and friability as compared with compositions of choline salicylate-metal salicylate plus MCC alone or choline salicylate-metal salicylate-metal carboxymethylcellulose alone. As indicated above, improved tablet performance is noted when the MCC forms a liquid bridge with the composition, which can be best accomplished by the addition of both CMC and MCC to the solution with the choline salicylate and metal salicylate entities before solvent evaporation or upon incorporation of MCC with the choline salicylate-metal salicylate-carboxymethylcellulose composition in powder form before wet granulation. Dry blending of MCC with choline salicylate-metal salicylate-CMC after this composition is wet granulated will not result in improved tablet performance.

DESCRIPTION OF PREFERRED EMBODIMENTS

The following examples are given to further illustrate the present invention. The scope of the invention is not, however, meant to be limited to the specific details of the examples.

EXAMPLE 1

An aqueous solution of Choline Magnesium Salicylate with Carboxymethylcellulose (CMC) is prepared according to U.S. Pat. No. 4,067,974 with microcrystalline cellulose (MCC) incorporated in a slurry with the following ingredients:

|  | % |
| --- | --- |
| Water Deionized | 47.9606 |
| Cellulose Gum | 1.3288 |
| Salicylic Acid USP Cryst. | 0.5753 |
| Disodium EDTA | 0.0164 |
| Choline Dicarbonate* | 12.8219 |
| Salicylic Acid USP Cryst. | 32.1644 |
| Magnesium Hydroxide** | 4.5342 |
| Water Deionized | qs. ad. |
| Microcrystalline Cellulose | % desired (wt. of solution × 45% (kg) |

*Amount based on assay
**Amount based on assay

The amount of microcrystalline cellulose incorporated as a slurry is based on the weight of the above solution containing 45% solids.

The solvent is evaporated using a spray dryer until a dry powder is obtained. The resultant powder is then granulated to form a larger particle size by moistening with isopropyl alcohol and water according to the following formula.

|  | % |
| --- | --- |
| MCT (Magnesium Choline Trisalicylate) W/SD (Spray Dried) MCC | 82.6 |
| Isopropyl Alcohol (USP) | 11.3 |
| Purified Water | 3.3 |
| Stearic Acid | 2.0 |
| Talc | .8 |

Step 1: Charge appropriate mixer with 82.62% MCT Powder w/SD MCC.
Step 2: Blend for 5 minutes.
Step 3: Heat mixing vessel to 30°-40° C.
Step 4: Incorporate 11.3% isopropyl alcohol and 3.3% purified water while mixing
Step 5: Post mix for an appropriate length of time until an endpoint of the moist granular mass is reached. If necessary add additional water to reach an endpoint of a moist granular mass.
Step 6: Dry the granulation to 0.8% LOD or less or 6PPM IPA or less.
Step 7: Mill the granulation to approximately 10-15% through 325 mesh using the equivalent of a 0.050 screen.
Step 8: Charge appropriate mixer vessel with milled granulation from step 7.
Step 9: Add enough purified water to reach a granulate LOD in the range of 2.5-3.5%. Step 10: Post mix for 5 minutes.
Step 11: Mill the granulation to approximately 10-15% through 325 325 mesh using the equivalent of a 0.050 screen.
Step 12: Lubricate the batch using appropriate amounts of stearic acid and talc.

Once the granulation is made, compress into tablets of 1173.2 mg, equivalent to 750 mg salicylate, and 1564.3 mg, equivalent to 1000 mg, of salicylate.

Prepare a second batch of CMT Powder as per U.S. Pat. No. 4,067,974 as above but without the microcrystalline cellulose. Compress into tablets as above.

All tablets were tested for hardness using a Schleuniger hardness tester and friability using the Roche Type Friabiliator. (Lachman, Liebeman, Kanig, The Theory and Practice of Industrial Pharmacy 3rd Ed. pp. 88,299).

The above mentioned formula represents Choline Magnesium Trisalicylate with 7.5% MCC per weight MCT powder. Tablet weights for a formula containing 10% MCC per weight MCT powder yield tablets of 11.99.6 mg equivalent to 750 mg of salicylate, and 1599.5 mg, equivalent to 1000 mg of salicylate.

Results:

| Strength (Salicylate) | % MCC | % CMC | Hardness | Friability |
| --- | --- | --- | --- | --- |
| CHOLINE MAGNESIUM TRISALICYLATE TABLETS WITH MICROCRYSTALLINE CELLULOSE | | | | |
| 750 mg | 7.5% | 2.6 | 20 kp+ | Passed-no chips |
| 750 mg | 10% | 2.6 | 20 kp+ | Passed-no chips |
| 1000 mg | 7.5 | 2.6 | 20 kp+ | Passed-no chips |
| 1000 mg | 10.0% | 2.5 | 20 kp+ | Passed-no chips |
| CHOLINE MAGNESIUM TRISALICYLATE TABLETS WITHOUT MICROCRYSTALLINE CELLULOSE | | | | |
| 750 mg | — | 2.6 | 11.9 kp | Failed-4 broken tablets |
| 1000 mg | — | 2.6 | 16.4 kp | Failed-3 broken tablets |

The results above show that tablets with 7.5% and 10% microcrystalline cellulose display enhanced tablet performance in terms of hardness and friability over tablets with no MCC.

EXAMPLE 2

Prepare an aqueous solution of choline magnesium salicylate with carboxymethylcellulose (CMC) according to U.S. Pat. No. 4,067,974 with the following ingredients:

|  | % |
| --- | --- |
| Water Deionized | 47.9606 |
| Cellulose Gum | 1.3288 |
| Salicylic Acid USP Cryst. | 0.5753 |
| Disodium EDTA | 0.0164 |
| Choline Bicarbonate* | 12.8219 |
| Salicylic Acid USP Cryst. | 32.1644 |
| Magnesium Hydroxide** | 4.5342 |
| Water Deionized | qs.ad. |

*Amount based on assay
**Amount based on assay

Evaporate the solvent using a spray dryer until a dry powder is obtained. The resultant powder is then granulated with microcrystalline cellulose to form a larger particle size by moistening with isopropyl alcohol and water following these formulas:

| FORMULA (A) CHOLINE MAGNESIUM TRISALICYLATE WITH 7.5% MCC PER WEIGHT MCT POWDER | |
| --- | --- |
|  | % |
| MCT Powder | 76.6 |
| Microcrystalline Cellulose | 5.7 |
| Isopropyl Alcohol (USP) | 11.4 |
| Purified Water | 3.4 |
| Purified Water | qs. |
| Stearic Acid | 2.1 |

FORMULA (A)
CHOLINE MAGNESIUM TRISALICYLATE WITH 7.5% MCC PER WEIGHT MCT POWDER

|  | % |
|---|---|
| Talc | .8 |

FORMULA (B)
CHOLINE MAGNESIUM TRISALICYLATE WITH 10% MCC PER WEIGHT MCT POWDER

|  | % |
|---|---|
| MCT Powder | 75.2 |
| Microcrystalline Cellulose | 7.5 |
| Isopropyl Alcohol (USP) | 11.2 |
| Purified Water | 3.2 |
| Purified Water | qs. |
| Stearic Acid | 2.1 |
| Talc | .8 |

Use the following procedure for both formulas:

Step 1: Charge appropriate mixer with MCT powder and microcrystalline cellulose.
Step 2: Blend for 5 minutes.
Step 3: Heat mixing vessel to 30° C.–40° C.
Step 4: Incorporate isopropyl alcohol and purified water while mixing.
Step 5: Post mix for an appropriate length of time until an endpoint of a moist granular mass is reached. If necessary, add additional water to reach an endpoint of a moist granular mass.
Step 6: Dry the granulation to 0.8% LOD or less or 6PPM IPA or less.
Step 7: Mill the granulation to approximately 10–15% through 325 mesh using the equivalent of a 0.05 screen.
Step 8: Charge appropriate mixer vessel with milled granulation from Step 7.
Step 9: Add enough purified water to reach a granulate LOD in the range of 2.5–3.5%.
Step 10: Post mix for 5 minutes.
Step 11: Mill the granulation to approximately 10–15% through 325 mesh using the equivalent of a 0.050 screen
Step 12: Lubricate the batch using appropriate amounts of stearic acid and talc.

Once the granulations are made, compress Formula A granulation into tablets of 11173.2 mg, equivalent to 750 mg salicylate, and 1564.3 mg, equivalent to 1000 mg of salicylate. Compress Formula B granulation into tablets of 1199.6 mg equivalent to 750 mg salicylate, and 1599.5 mg, equivalent to 1000 mg of salicylate.

Prepare a second batch of CMT Powder according to U.S. Pat. No. 4,067,974 as above but without the microcrystalline cellulose. Compress into tablets as above.

All tablets were tested for hardness and friability as in Example 1.

Results:

| Strength (Salicylate) | % MCC | % CMC | Hardness | Friability |
|---|---|---|---|---|
| FORMULA (A) CMT TABLETS WITH 7.5% MCC ||||||
| 750 mg | 7.5% | 2.6 | 20 kp+ | Passed |
| 1000 mg | 7.5% | 2.6 | 20 kp+ | Passed |
| FORMULA (B) CMT TABLETS WITH 10% MCC |||||
| 750 mg | 10.0% | 2.6 | 20 kp+ | Passed |
| 1000 mg | 10.0% | 2.6 | 20 kp+ | Passed |
| CMT TABLETS WITHOUT MCC |||||
| 750 mg | — | 2.6 | 12.6 kp | Failed-large chips-tabls. broken |
| 1000 mg | — | 2.6 | 15 kp | Failed-severe erosion |

The results of these tablets were then compared to the results of Example 1. It was shown that 7.5% microcrystalline cellulose is as effective as 10% microcrystalline cellulose. In addition, incorporation of MCC into Choline Magnesium Trisalicylate as per Examples 1 and 2 enhance hardness and friability.

EXAMPLE 3

Prepare an aqueous solution of Choline Magnesium Salicylate with Carboxymethylcellulose (CMC) according to Patent No. 4,067,974 with microcrystalline cellulose (MCC) incorporated in a slurry as per Example 1. The amount of microcrystalline cellulose incorporated as a slurry is based on the weight of the above solution containing 45% solids. Incorporate 5% MCC as a slurry as in Example 1.

Evaporate the solvent using a spray dryer until a dry powder is obtained. The resultant powder is then granulated to form a larger particle size. Once the granulation is made, compress into tablets of 1529 mg, equivalent to 1000 mg of salicylate.

All tablets were tested for hardness using a Schleuniger harness tester and friability using the Roche type Friabiliator. (Lachman, Lieveman, Kanig, The Theory and Practice of Industrial Pharmacy 3rd Ed. pp. 88,299).

Results:
CHOLINE MAGNESIUM TRISALICYLATE TABLETS MICROCRYSTALLINE CELLULOSE

| Strength (Salicylate) | % MCC | % CMC | Hardness | Friability |
|---|---|---|---|---|
| 1000 mg | 5% | 2.6 | 20 kp | Capped Tabls. |

Results indicate that 5% MCC is not quite as effective in enhancing tabletting performance as compared to CMT tablets with CM/MCC from Example 1 and 2.

EXAMPLE 4

Prepare an aqueous solution of Choline Magnesium Salicylate with Carboxymethylcellulose (CMC) according to U.S. Pat. No. 4,067,974 with microcrystalline cellulose (MCC) incorporated in a slurry as per Example 1. The amount of MCC incorporated as a slurry is based on the weight of the above mentioned solution containing 45% Solids. Therefore, prepare a solution with 7.5% MCC and another with 10% MCC.

Evaporate the solvent using a spray dryer until a dry powder is obtained. The resultant powder is then granulated to form a larger particle size by moistening with isopropyl alcohol and water according to the following formula:

|  | % |
|---|---|
| MCT Powder w/SD MCC | 82.6 |
| Isopropyl Alcohol (USP) | 11.3 |
| Purified Water | 3.3 |
| Purified Water | qs. |
| Stearic Acid | 2.0 |
| Talc | 0.8 |

The manufacturing procedure is as in Example 1. The granulation of Choline Magnesium Trisalicylate with 7.5% MCC per weight of MCT Powder is compressed into tablets of 1173.2 mg, equivalent to 750 mg salicylate, and 1564.3 mg, equivalent to 1000 mg of salicylate. The granulation of Choline Magnesium Trisalicylate with 10% MCC per weight of MCT Powder is compressed into tablets of 1199.6 mg equivalent to 750 mg of salicylate, and 1599.5 mg, equivalent to 1000 mg of salicylate.

Prepare a third and fourth batch of CMT powder in the same manner as above using 7.5% MCC in the third batch and 10% MCC in the fourth batch but without the carboxymethylcellulose (CMC). Compress into tablets as above.

All tablets were tested for hardness and friability as in Example 1.

Results:

| Strength (Salicylate) | % MCC | % CMC | Hardness | Friability |
|---|---|---|---|---|
| CMT TABLET WITH MICROCRYSTALLINE CELLULOSE AND CMC | | | | |
| 750 mg | 7.5% | 2.6 | 20 kp+ | Passed-no chips |
| 750 mg | 10% | 2.6 | 20 kp+ | Passed-no chips |
| 1000 mg | 7.5% | 2.6 | 20 kp− | Passed-no chips |
| 1000 mg | 10% | 2.6 | 20 kp+ | Passed-no chips |
| CMT TABLETS WITH MICROCRYSTALLINE CELLULOSE AND NO CMC | | | | |
| 750 mg | 7.5% | — | 17-20 kp | Failed/11 broken tab. |
| 750 mg | 10% | — | 20 kp | Failed/4 broken tab. |
| 1000 mg | 7.5% | — | 20 kp | Failed/3 major chips Erosion of edges |
| 1000 mg | 10% | — | 20 kp | Failed/3 major chips Erosion of edges |

The results show that Choline Magnesium Trisalicylate tablets made from granulations with the combination of microcrystalline cellulose and carboxymethylcellulose all passed friability testing whereas tablets made from granulations with microcrystalline cellulose alone failed friability testing.

This proves that the incorporation of MCC/CMC in Choline Magnesium Salicylate enhances tablet performance in terms of friability.

EXAMPLE 5

Prepare two aqueous solutions of Choline Magnesium Salicylate with Carboxymethylcellulose (CMC) as in Example 2.

Evaporate the solvent, using a spray dryer until a dry powder is obtained. The resultant powder is then granulated with microcrystalline cellulose to form a larger particle size by moistening with isopropyl alcohol and water following these formulas.

|  | % |
|---|---|
| FORMULA (A) CMT WITH A 2.6% CMC AND 7.5 MCC | |
| MCT Powder with CMT | 76.6 |
| Microcrystalline Cellulose | 5.7 |
| Isopropyl Alcohol (USP) | 11.4 |
| Purified Water | 3.4 |
| Purified Water | qs. |
| Stearic Acid | 2.1 |
| Talc | 0.8 |
| FORMULA (B) CMT WITH A 2.6% CMC AND 10% MCC | |
| MCT Powder with CMT | 75.2 |
| Microcrystalline Cellulose | 7.5 |
| Isopropyl Alcohol (USP) | 11.2 |
| Purified Water | 3.2 |
| Purified Water | qs. |
| Stearic Acid | 2.1 |
| Talc | 0.8 |
| FORMULA (C) CMT WITH NO CMC AND 7.5% MCC | |
| MCT Powder with CMT | 76.2 |
| Microcrystalline Cellulose | 5.7 |
| Isopropyl Alcohol (USP) | 11.4 |
| Purified Water | 3.4 |
| Purified Water | qs. |
| Stearic Acid | 2.1 |
| Talc | 0.8 |
| FORMULA (D) CMT WITH NO CMC AND 10% MCC | |
| MCT Powder with CMT | 75.2 |
| Microcrystalline Cellulose | 7.5 |
| Isopropyl Alcohol (USP) | 11.2 |
| Purified Water | 3.2 |
| Purified Water | qs. |
| Stearic Acid | 2.1 |
| Talc | 0.8 |

The manufacturing procedure for all four formulas is as in Example 2. Once the granulations are made, compress Formula A granulation into tablets of 1173.2 mg, equivalent to 750 mg salicylate, and 1564.3 mg, equivalent to 1000 mg of salicylate. Compress formula B granulation into tablets of 1199.6 mg, equivalent to 750 mg salicylate, and 1599.5 mg, equivalent to 1000 mg of salicylate. Formula C granulation is compressed into tablets equivalent to Formula A. Formula D granulation is compressed into tablets equivalent to Formula B.

All tablets were tested for hardness and friability as in Example 1.

Results:

| Strength (Salicylate) | % MCC | % CMC | Hardness | Friability |
|---|---|---|---|---|
| FORMULA (A) CMT TABLETS WITH 2.6% CMC & 7.5% MCC | | | | |
| 750 mg | 7.5% | 2.6 | 20 KP+ | Passed |
| 1000 mg | 10% | 2.6 | 20 KP+ | Passed |
| FORMULA (B) CMT TABLETS WITH 2.6% CMC & 10% MCC | | | | |
| 750 mg | 10% | 2.6 | 20 KP+ | Passed |
| 1000 mg | 10% | 2.6 | 20 KP+ | Passed |
| FORMULA (C) CMT TABLETS NO CMC & 7.5% MCC | | | | |
| 750 mg | 7.5% | — | 17-20 KP | 15 Broken tabs. Failed. |
| 1000 mg | 7.5% | — | 20 KP | Failed-3 major chips, erosion. |
| FORMULA (D) CMN TABLETS NO CMC 10% MCC | | | | |
| 750 mg | 10% | — | 17-20 KP | Failed-1 broken tablet, 4 major chips |
| 1000 mg | 10% | — | 20 KP | Failed-5 chipped |

| Results: Strength (Salicylate) | % MCC | % CMC | Hardness | Friability |
|---|---|---|---|---|
| | | | | tablets, erosion. |

The results of these tablets were then compared to the results Example 4. It was shown that 7.5% microcrystalline cellulose is as effective as 10% microcrystalline cellulose. In addition, the combination of CMC/MCC in choline magnesium trisalicylate tablets enhances hardness and friability.

EXAMPLE 6

Prepare two aqueous solutions of Choline Magnesium Salicylate with Carboxymethylcellulose (CMC) as in Example 2.

Evaporate the solvent, using a spray dryer, until a dry powder obtained. The resultant powder is then granulated following this formula.

| | % |
|---|---|
| MCT Powder | 82.6 |
| Isopropyl Alcohol (USP) | 11.3 |
| Purified Water | 3.3 |
| Purified Water | qs. |
| Stearic Acid | 2.0 |
| Talc | 0.8 |

The manufacturing procedure is as in Example 1. Once the granulation is made, incorporate microcrystalline cellulose 15% and dry blend for five minutes. The granulation of Choline Magnesium Trisalicylate with 15% MCC per weight of MCT powder is compressed into tablets of approximately 1252 mg equivalent to 750 mg salicylate. Table were tested for hardness and friability as in Example 1.

Results:
CMT TABLETS WITH DRY BLENDED MCC

| Strength (Salicylate) | % MCC | % CMC | Hardness | Friability (3 Min) |
|---|---|---|---|---|
| 750 mg | 15% | 2.6 | 10.5 kp | Failed-severe erosion |
| 750 mg | 15% | 2.6 | 10.5 kp | Failed-severe erosion. |

The results of this experiment show that even at a level of 15% MCC incorporated in a dry blend does not produce tablets with the same hardness and friability as tablets produced in Examples 1 and 2 in which 7.5% MCC was incorporated either as a slurry or before wet granulation. This proves that stabilization of Choline Magnesium Salicylate with MCC occurs at relatively lower levels (7.5%) when microcrystalline cellulose is incorporated during the formation of the choline metal carboxymethylcellulose salicylate compound, (Example 1), or before wet granulation of the primary choline metal carboxymethylcellulose salicylate (Example 2).

EXAMPLE 7

Prepare an aqueous solution of Choline Magnesium Salicylate with Carboxymethylcellulose (CMC) as in Example 2. Evaporate the solvent using a spray dryer until a dry powder is obtained. The resultant powder is then divided into 6 portions and each portion is then granulated with the following binding agents:
a. Hydroxypropylmethylcellulose (E5 Prem. Grade).
b. Povidone C 30 (PVP)
c. Polymethacrylate
d. Cross Linked Povidone (Plasdone XL)
e. Glycerin
f. Stearic Acid.

The above materials were incorporated at levels usually used binding agents in pharmaceutical granulations.

The formulae utilizing the above agents are as follows:

| Ingredients | Formula A % | Formula B % | Formula C % | Formula D % | Formula E % | Formula F % |
|---|---|---|---|---|---|---|
| MCT Powder | 88.4 | 87.7 | 88.4 | 87.0 | 95.7 | 96.5 |
| HPMC | 8.4 | — | — | — | — | — |
| PVP | — | 9.1 | — | — | — | — |
| Polymethacrylate | — | — | 8.4 | — | — | — |
| PVP (Cross linked) | — | — | — | 9.9 | — | — |
| Glycerin | — | — | — | — | 0.9 | — |
| Stearic Acid | — | — | — | — | — | 2.5 |
| IPA/Water | 7:1 | 8:2 | — | 7:1 | 7:1 | 6:1 |
| Talc (Lubrication) | 0.9 | 0.9 | 0.9 | 0.9 | 1.0 | 1.0 |
| Stearic Acid (Lubrication) | 2.3 | 2.3 | 2.3 | 2.3 | 2.4 | — |

The procedure of manufacturing formula A, B, D and F is as per Example 2. Microcrystalline Cellulose is omitted and the appropriate binding agent is used. Formula C utilizes polymethylacrylate in suspension form and is incorporated in the granulation step. Formula E includes glycerin added in isopropyl alcohol which is then used for granulating as per Example 2. In all formulas MCC is not used.

Once the granulations are made, compress all granulations to tablet weights in the range of 1150 mg to 1200 mg, equivalent to approximately 750 mg salicylate, and 1550 mg to 1600 mg equivalent to approximately 1000 mg salicylate. All tablets were tested for hardness and friability as in Example 1.

Results:

| Strength (Salicylate) | Hardness | Friability | Observations |
|---|---|---|---|
| FORMULA (A) CMT TABLETS WITH HPMC 8.4% W/W PER TABLET | | | |
| 1000 mg | 20 kp | Failed capped tablets | Sticky tablets |
| FORMULA (B) CMT TABLETS WITH PVP 9.1% W/W PER TABLET | | | |
| 1000 mg | 17-19 kp | Failed erosion | Tablet friability increased with time |
| FORMULA (C) CMT TABLETS WITH POLYMETHACRYLATE 8.4% W/W PER TABLET | | | |
| — | — | — | Polymethacrylate renders granulation |

-continued

| Results: Strength (Salicylate) | Hardness | Friability | Observations |
|---|---|---|---|
| FORMULA (D) CMT TABLETS WITH PVP (CROSS LINKED) 9.9 W/W PER TABLET | | | too sticky to process. |
| 750 mg | <12 kp | Failed capped tablets | Tablets too soft |
| FORMULA (E) CMT TABLETS WITH GLYCERIN 0.9% W/W PER TABLET | | | |
| 750 mg | — | — | Sticking occurred along with picking |
| FORMULA (F) CMT TABLETS WITH STEARIC ACID 2.5% W/W PER TABLET | | | |
| 750 mg | 10 kp | Failed | Tablets too soft. |

The results here show that the agents used above failed to provide improved tablet performance. The results of these tablets were then compared to the results of Example 2 with tablets containing 7.5% MCC with 2.6% CMC. Thus, the use of other common pharmaceutical solid dosage binder, such as povidone, acrylic resins, methocel and fatty acids did not enhance the tabletting performance of the primary composition.

Attempts were made to improve CMT granulation with 2.6% CMC by incorporating glyceryl behenate (Compritol HDS and 888ATD at 3% w/w levels. Prior to addition of these agents, tablets produced from these granulations were soft and friable. Compression results on these granulations with these agents showed no improvement in hardness or friability. Similar results were evident when attempts were made to improve CMT granulation performance by incorporating hydrogenated vegetable oil at 5% w/w levels.

While the invention has been described with respect to particular formulations, it is apparent that variations and modifications of the invention can be made without departing from the spirit or scope thereof.

What is claimed is:

1. Stabilized solid composition comprising choline salicylate, a stabilizing amount of the salicylate of at least one physiologically compatible metal having a valence of at least 2, a stabilizing effective amount of a carboxy lower alkyl cellulose, and a stabilizing amount of microcrystalline cellulose linked to the remainder of the composition by way of liquid bridges, which amount stabilizes the composition and thus enhances the stability of solid dosage forms of said composition.

2. Composition according to claim 1 wherein said lower alkyl cellulose is carboxy methyl cellulose.

3. Composition according to claim 1 wherein said carboxy lower alkyl cellulose is present in an amount of about 2.5–25% by weight.

4. Composition according to claim 3 wherein said carboxy lower alkyl cellulose is carboxymethyl cellulose.

5. Composition according to claim 1 wherein said microcrystalline cellulose is present in an amount of about 2.5–25% by weight.

6. Composition according to claim 5 wherein said carboxy lower alkyl cellulose is carboxymethyl cellulose.

7. Composition according to claim 3 wherein the amount of microcrystalline cellulose is about 2.5–25% by weight.

8. Composition according to claim 7 wherein said carboxy lower alkyl cellulose is carboxymethylcellulose.

9. Composition according to claim 1 wherein metal is aluminum, bismuth, calcium or magnesium.

10. Composition according to claim 1 in the form of a tablet, capsule, suppository or granule.

11. Composition according to claim 3 wherein said metal is aluminum, bismuth, calcium or magnesium.

12. Composition according to claim 3 in the form of a tablet, capsule, suppository or granules.

13. Composition according to claim 7 wherein said metal is aluminum, bismuth, calcium or magnesium.

14. Composition according to claim 7 in the form of a tablet, capsule, suppository or granules.

15. Composition according to claim 1 wherein the particle size of said microcrystalline cellulose is between about 16 mesh and 400 mesh.

16. Composition according to claim 3 wherein the particle size of said microcrystalline cellulose is between about 60 mesh and 400 mesh.

17. Composition according to claim 5 wherein the particle size of said microcrystalline cellulose is between about 60 mesh and 400 mesh.

18. Composition according to claim 7 wherein the particle size of said microcrystalline cellulose is between about 60 mesh and 400 mesh.

19. Method of producing a stabilized solid composition comprising choline salicylate, a stabilizing amount of the salicylate of at least one physiologically compatible metal having a valence of at 2, a stabilizing effective amount of a carboxy lower alkyl cellulose, and a stabilizing amount of microcrystalline cellulose, which comprises mixing said microcrystalline cellulose with at least one of the choline salicylate or the salicylate of the physiologically compatible metal having a valence of at least 2 under wet conditions whereby liquid bridges are formed between the microcrystalline cellulose and the remainder of the composition, which amount stabilizes the composition and thus enhances the stability of solid dosage forms of said composition.

20. Method according to claim 19 wherein the microcrystalline cellulose is mixed under wet conditions with the choline salicylate, the metal salicylate of the metal having a valence of at least 2 and the carboxy lower alkyl cellulose.

21. Method according to claim 19 wherein the microcrystalline cellulose is granulated under wet conditions with metal-choline-trisalicylate formed from the choline salicylate and the metal salicylate.

* * * * *